(12) United States Patent
Chimenti et al.

(10) Patent No.: US 8,311,955 B2
(45) Date of Patent: Nov. 13, 2012

(54) BOOTSTRAP METHOD FOR OIL PROPERTY PREDICTION

(75) Inventors: Robert J. Chimenti, Short Hills, NJ (US); Patricia H. Kalamaras, Milford, NJ (US); Robert J. Pottorf, Houston, TX (US); Bruce N. Perry, Flemington, NJ (US)

(73) Assignee: ExxonMobil Research and Engineering Company, Annandale, NJ (US)

(*) Notice: Subject to any disclaimer, the term of this patent is extended or adjusted under 35 U.S.C. 154(b) by 620 days.

(21) Appl. No.: 12/287,673

(22) Filed: Oct. 10, 2008

(65) Prior Publication Data
US 2009/0119244 A1 May 7, 2009

Related U.S. Application Data

(60) Provisional application No. 61/000,966, filed on Oct. 30, 2007.

(51) Int. Cl.
*G06F 15/18* (2006.01)
(52) U.S. Cl. .......................................................... 706/12
(58) Field of Classification Search .................. None
See application file for complete search history.

(56) References Cited

U.S. PATENT DOCUMENTS

| | | | |
|---|---|---|---|
| 5,121,337 A * | 6/1992 | Brown ............................ 702/28 |
| 5,360,972 A * | 11/1994 | DiFoggio et al. ......... 250/339.12 |
| 5,412,581 A * | 5/1995 | Tackett ............................ 702/30 |
| 5,424,959 A * | 6/1995 | Reyes et al. ..................... 702/28 |
| 5,668,374 A * | 9/1997 | DiFoggio et al. ........ 250/339.12 |
| 5,699,269 A * | 12/1997 | Ashe et al. ....................... 702/30 |
| 6,534,318 B2 * | 3/2003 | Roussis et al. ................ 436/139 |
| 6,549,861 B1 * | 4/2003 | Mark et al. ....................... 702/76 |
| 6,662,116 B2 * | 12/2003 | Brown ............................ 702/22 |
| 7,223,603 B2 | 5/2007 | Rovani, Jr. et al. |
| 2006/0136149 A1 | 6/2006 | Long et al. |
| 2006/0142955 A1 | 6/2006 | Jones et al. |
| 2010/0174494 A1 * | 7/2010 | De Peinder et al. ............ 702/30 |

OTHER PUBLICATIONS

Divya, O. et al.; "Combining synchronous fluorescence spectroscopy withmultivariate methods for the analysis of petrol-kerosene mixtures"; Mar. 2007; Talanta, vol. 72, No. 1; pp. 43-48.*

Divya, O. et al.; "Multivariate methods on the excitation emission matrix fluorescence spectroscopc data of diesel-kerosene mixtures: A comparative study"; May 2007; Analytica Chimica Acta, vol. 592, No. 1; pp. 82-90.*

* cited by examiner

*Primary Examiner* — Jeffrey A. Gaffin
*Assistant Examiner* — Stanley K Hill
(74) *Attorney, Agent, or Firm* — Ronald D. Hantman; Glenn T. Barrett

(57) ABSTRACT

The present invention is a method to determine models to predict physical or chemical properties of a petroleum fluid when such properties of such fluids cannot be measured by conventional analytical methods. The invention includes the steps of determining one or more models that predict one or more predetermined properties from a set of oils whose optical spectra and properties are known wherein a model corresponds to each predetermined property which is related to the spectrum, estimating the quality of the models, estimating the predictive quality for samples with unknown properties, augmenting the spectrum with shape parameters and/or properties that are predicted by the step above, and determining the quality and predictive quality of the models. The models are then used to predict properties of very small samples.

11 Claims, No Drawings

BOOTSTRAP METHOD FOR OIL PROPERTY PREDICTION

This application claims the benefit of U.S. Provisional Application 61/000,966 filed on Oct. 30, 2007.

BACKGROUND OF THE INVENTION

The present invention is a method to develop models to predict physical and chemical properties of petroleum hydrocarbon fluids from their optical spectra.

The model is then used to determine these physical and chemical properties of fluids that may not be present or accessible in sufficient quantity to measure the properties by conventional analytical methods.

One use of the invention is the non-destructive prediction of the chemical and physical properties of picoliter quantities of petroleum fluids trapped in inclusions in quartz and carbonate minerals and cements from only the measurement of the fluid's fluorescence spectrum. A second use is the prediction of the properties of hydrocarbon fluids that are remote from the measuring apparatus and, therefore, not able to be acquired or isolated non-destructively from their environment. Thus, the prediction of the properties of hydrocarbon fluid stains or thin layers on rocks or water from the remote measurement of the hydrocarbon fluorescence are examples. Logging of predicted fluid properties using down hole fluorescence probes is a third example.

SUMMARY OF THE INVENTION

The present invention includes a method to develop models to predict chemical and physical properties of a hydrocarbon fluid from its spectrum.

The method for developing the models include the following steps:

determining one or more models that predict one or more predetermined properties from a set of oils whose optical spectra and properties are known wherein a model corresponds to each predetermined property and which is obtained from the spectrum, determining the quality of the models to estimate the property values of the known oils, estimating the predictive quality for samples with unknown property values, augmenting the spectrum with spectrum shape parameters and/or predicted properties and again determining the quality and predictive quality of the models. By "quality" is meant the accuracy, precision, reliability, and speed of measurement, together or in combination.

In a preferred embodiment the model may include the further step of again augmenting the input to the models with the predicted properties to further improve the quality and the predictive quality of the models.

The invention also includes a method to use the models to predict physical and chemical properties of petroleum hydrocarbon fluids from their optical spectra when such fluids are not accessible, not in sufficient quantity, or not in a physical or chemical state for the application of conventional analytical techniques. The invention has the further advantage of determining multiple oil properties from a single sample, rapidly and at relatively low cost, since all of the properties of interest are determined from the single measurement of the sample spectrum.

Methods to develop mathematical models to predict properties of a material from its near- and mid-infrared absorption spectra, for example, are known in the art. It is also known in the art that augmenting the spectrum with other measured material properties can improve prediction quality. However, in the applications cited, measured properties, other than the spectra, are not obtainable.

It has been shown in the present invention that certain properties of a hydrocarbon fluid can be estimated and predicted to greater accuracy than other properties from its fluorescence spectrum. Prediction of these certain properties may be further improved by models using as input the spectrum augmented by certain parameters of the spectrum. It has further been shown that these certain properties may correlate with other properties of interest that are less accurately predicted. The invention improves the prediction quality of the less accurately predicted properties of a sample by iteratively augmenting its spectrum and spectrum-derived parameters by the predictions of the properties that are more accurately predicted as inputs to multiple stage models. The method of iterative augmentation and prediction is referred to as a "bootstrap" method.

DETAILED DESCRIPTION OF THE PREFERRED EMBODIMENT

The present invention includes the development of models to predict chemical and physical properties of hydrocarbon fluids from their spectrum with no additional measurements or characterization.

The accuracy of certain properties of a hydrocarbon fluid predicted from its spectrum can be improved when spectrum-derived parameters, in combination with the spectrum, together called first-stage variables, are used as input to prediction models. The predicted values for the properties are called first-stage predictions. Further improvements to the predictions may be realized from second-stage models that use as input variables all of the first stage variables and property predictions, together called the second-stage variables. The predicted properties from the second-stage models are called the second stage predictions. This process can be iterated further. Means are provided, at each model-building stage for each property, to determine, from the input variables, those that meet statistical criteria for improvement to the predictions. This multi-stage "bootstrap" prediction methodology is applied and tested on each property of interest.

The final models are then used for the prediction of properties of oils trapped in micron-size inclusions that are formed in optically transparent minerals and cements, such as quartz and carbonates, as examples. Examples of such predicted properties of interest are API gravity, Conradson Carbon, viscosity, and the percentage by weight, wt. %, of total sulfur, aromatics, saturates, and oil having boiling point temperatures greater than 1050° F. (called the % Residuum or Resid Yield). The optical spectrum in this example is the fluorescence spectrum.

A variety of modeling techniques and their combinations can be used to relate the spectrum of a sample to its physical or chemical properties of interest, a few examples of such techniques being Principal Component Regression, Pattern Recognition, Classification, and Spectral Matching methods. The invention will be further described using Stepwise Principal Component Regression as the model building method. For the example considered, these techniques require a fluorescence spectrum for each oil sample and the corresponding known values of the properties of interest, for a set of representative samples. Crude oil is used to simulate inclusion oils. These are called the calibration samples, and should be of sufficient number so as to span the variability exhibited by each of the properties of interest over their respective range of interest. The modeling technique is used to establish quantitative relationships between the spectrum and the properties of interest for each of the samples in the calibration set. One measure of the estimation quality of the calibration model is the Standard Error of Calibration (SEC). A "leave one out" Cross Validation method can be used to estimate the prediction quality of the model when applied to samples with unknown properties. One such quantification is the Standard Error of Cross-Validation (SECV). Generally, these modeling methodologies and statistical metrics are known in the art. The instant invention is applicable to any model methodology.

The invention includes the following steps to develop the model using the spectrum as the only measured property of the oil:

Spectrum pre-treatment: The measured fluorescence spectrum from an oil-bearing inclusion may be pre-treated prior to being used as input to property prediction models. Generally, the as-measured intensity information is not useful in the models since mechanisms other than the chemical and physical properties of the sample, such as focusing, scattering, and absorption can significantly affect the detected intensity. Consequently, each spectrum can be normalized to its peak value or to unit area, as two examples of pre-treatment methods.

First-stage predictions: In the first stage, individual models are developed to predict each property of interest using, as input, information only from the pre-treated spectrum obtained from the set of characterized samples that are to be used for calibration. The input information from the pre-treated spectrum consist of any or all of the following: the amplitude at selected wavelengths, the full spectrum, the centroid, full width at half maximum, skewness, area, and other derived moments and characteristics of the spectrum. These spectrum parameters can be used individually or in combination, weighted by different amounts, and such parameters and weights may be different for each property model. In the present example, the full spectrum is used for each model in combination with spectrum-derived parameters. The combined parameters and their weights to be used as inputs to the models comprise the first-stage variables. The values of the properties that are predicted from these variables are called the first-stage predictions and the models called the first-stage models.

Second-stage predictions: In the second stage, additional models are developed to again predict each of the properties of interest but now using the full or partial set of both first-stage variables and first-stage predicted properties in combination, called the second-stage variables, as the model input variables for each property of interest. The values that are predicted using these variables are called the second-stage predictions and the models called the second-stage models. The first and second stage of predictions are compared and the best prediction for each of the properties of interest is used to select the corresponding model for prediction of unknown samples.

This "bootstrap" process can continue until models for all of the properties of interest are obtained to the accuracy required for the application or until no further improvement is made. Each resulting final model may use different spectrum-derived parameters and predicted property inputs and their weights. Means are provided in the model-building methodology, to test if any of the spectrum or predicted property parameters that comprise the input variables at each stage, result in a statistically significant improvement to the prediction accuracy of a property of interest.

The method is demonstrated on a set of whole crude oils. The results are shown in Table 1. Seven properties are of interest and predicted from their fluorescence spectra with and without the Bootstrap Method. The properties are API Gravity, Resid Yield, ConCarbon, Viscosity, Total Sulfur, Aromatics, and Saturates. The modeling method used was Stepwise Principal Components Regression. An F-test with a p-value of 0.85 was used as the selection criteria for the addition of a new spectral or predicted property variable. Twenty principal components were specified. The following table shows the results of the Standard Errors of Calibration and Cross-Validation, SEC and SECV, respectively, of the models for the cases where: the properties were predicted using the full spectrum only, Column A, and the Bootstrap Method, Columns B and C. Column B shows the SEC and SECV using the first stage variables; that is, the full spectrum and spectrum-derived parameters. Column C shows the SEC using the second-stage variables; that is, the spectrum-derived parameters plus the first stage predictions. The table entries are in the form: SEC/SECV. Unity weightings were used for the input variables in this example.

It can be seen that the SEC of all of the properties are significantly improved (Column B) by the addition of the shape factors to the full spectrum input. The first four properties are further improved by the addition of the first-stage predictions to the first-stage variables. The final model qualities, for this example, are shown in the boxed values in columns B and C of the table. This model is then used to determine these properties for micron-size inclusions.

TABLE 1

Standard Errors Using Stepwise Principal Component Regression

| | A<br>Full Spectrum | | B<br>A + Shape<br>Parameters | | C<br>B + Predicted<br>Properties | |
|---|---|---|---|---|---|---|
| Property | SEC | SECV | SEC | SECV | SEC | SECV |
| API | 4.08 | 4.17 | 2.94 | 3.01 | 2.81 | 2.82 |
| Resid Yield | 3.85 | 3.99 | 3.10 | 3.19 | 3.02 | 3.03 |
| Con Carbon | 1.33 | 1.38 | 0.91 | 1.00 | 0.82 | 0.84 |
| Viscosity | 20.60 | 22.86 | 2.68 | 0.20 | 0.19 | 0.19 |
| Sulfur | 0.63 | 0.66 | 0.39 | 0.43 | no improvement | |
| Aromatics | 5.08 | 5.11 | 3.19 | 3.29 | no improvement | |
| Saturates | 5.52 | 5.64 | 3.54 | 3.67 | no improvement | |

Constraints: 20 components selected- use p = 0.85 in F-Test to add new variable

What is claimed is:

1. A method for developing models to predict physical and chemical properties of a petroleum fluid, comprising:
    (a) providing a fluorescence spectrum for each of a set of calibration samples of petroleum fluids, wherein each sample of petroleum fluid has known values of one or more preselected properties of interest, wherein the fluorescence spectrum for each of a set of calibration samples have one or more spectrum parameters;
    (b) developing a first stage model for each of the preselected properties of interest to predict such preselected properties of interest, wherein each first stage model being based on the fluorescence spectrum for each of the calibration samples, wherein the first stage model for each of the preselected properties of interest correlates to the same preselected property of interest for a calibration sample of the set of calibration samples with the spectrum of such calibration sample;
    (c) obtaining first-stage prediction properties from the first-stage models based upon first-stage variables obtained from the fluorescence spectrum and spectrum derived parameters for each of the set of calibration samples of petroleum fluids;

(d) developing a second-stage model for at least one of the preselected properties of interest to predict such preselected property of interest, wherein each second-stage model is based on the first-stage prediction properties and the first-stage variable for such preselected property of interest obtained from the first-stage model for such preselected property of interest; and (e) obtaining second-stage prediction properties from the second-stage models based upon second-stage variables obtained from the first-stage predicted properties and the first-stage variables.

2. The method of claim 1 wherein developing the first-stage model for each of the preselected properties of interest includes performing stepwise principal components regression.

3. The method of claim 1 wherein developing the second-stage model for at least one of the preselected properties of interest includes performing stepwise principal components regression.

4. The method of claim 1 wherein the one or more spectrum parameters includes at least one of the amplitude at selected wavelengths, the full spectrum, the centroid, full width at half maximum, skewness, area, and other derived moments and characteristics of the spectrum.

5. The method of claim 1, wherein the preselected properties of interest include one or more of API gravity, Conradson Carbon, viscosity, and weight percent of total sulfur, aromatics, saturates and resid yield.

6. The method of claim 1 wherein the set of calibration petroleum fluids are whole crude oils.

7. The method of claim 1, further comprising:
evaluating the quality of the first-stage model for a preselected property of interest compared to the second-stage model for the same preselected property of interest; and
selecting one of the first-stage model and the second-stage model for determining the preselected property of interest.

8. The method of claim 6, wherein evaluating the quality comprises using Standard Error of Calibration.

9. The method of claim 6, wherein evaluating the quality includes evaluating a predictive quality of the first-stage model for a preselected property of interest compared to the second-stage model for the same preselected property of interest.

10. The method of claim 8, wherein evaluating the predictive quality of the one or more developed models comprises using Standard Error of Cross-Validation.

11. A method for predicting one or more preselected properties of interest of an unknown sample of petroleum fluid, comprising:

obtaining one or more models from a set of calibration samples, comprising:

(a) providing a fluorescence spectrum for each of a set of calibration samples of petroleum fluids, wherein each sample of petroleum fluid has known values of one or more preselected properties of interest, wherein the fluorescence spectrum for each of a set of calibration samples have one or more spectrum parameters;

(b) developing a first stage model for each of the preselected properties of interest to predict such preselected properties of interest, wherein each first stage model being based on the fluorescence spectrum for each of the calibration samples, wherein the first stage model for each of the preselected properties of interest correlates to the same preselected property of interest for a calibration sample of the set of calibration samples with the spectrum of such calibration sample;

(c) obtaining first-stage prediction properties from the first-stage models based upon first-stage variables obtained from the fluorescence spectrum and spectrum derived parameters for each of the set of calibration samples of petroleum fluids;

(d) developing a second-stage model for at least one of the preselected properties of interest to predict such preselected property of interest, wherein each second-stage model is based on the first-stage prediction properties and the first-stage variable for such preselected property of interest obtained from the first-stage model for such preselected property of interest; and (e) obtaining second-stage prediction properties from the second-stage models based upon second-stage variables obtained from the first-stage predicted properties and the first-stage variables;

providing a fluorescence spectrum for the unknown sample having one or more spectrum parameters; and applying the fluorescence spectrum for the unknown sample in the first-stage model or the second-stage model for the preselected property of interest, thereby predicting the values of the preselected properties of interest of the unknown sample.

* * * * *